(12) United States Patent
Lawandy

(10) Patent No.: US 6,254,596 B1
(45) Date of Patent: Jul. 3, 2001

(54) SOLID STATE SOURCE FOR GENERATING INTENSE LIGHT FOR PHOTOMEDICINE

(75) Inventor: Nabil M. Lawandy, Providence, RI (US)

(73) Assignee: Spectra Science Corporation, Providence, RI (US)

( * ) Notice: Subject to any disclaimer, the term of this patent is extended or adjusted under 35 U.S.C. 154(b) by 0 days.

(21) Appl. No.: 09/103,453

(22) Filed: Jun. 24, 1998

Related U.S. Application Data

(63) Continuation-in-part of application No. 08/788,208, filed on Jan. 24, 1997, now Pat. No. 5,793,781.

(51) Int. Cl.$^7$ .................................................. A61B 18/18
(52) U.S. Cl. .................................... 606/9; 606/3; 372/22
(58) Field of Search ................................. 606/2, 3, 9, 10, 606/11, 13, 17; 372/3, 22, 39, 69, 92, 93

(56) References Cited

U.S. PATENT DOCUMENTS

| | | | |
|---|---|---|---|
| 4,733,660 | 3/1988 | Itzkan | 128/303.1 |
| 5,071,416 | * 12/1991 | Heller et al. | 606/3 |
| 5,112,328 | * 5/1992 | Taboada et al. | 606/4 |
| 5,163,061 | 11/1992 | Moberg | 372/29 |
| 5,217,455 | 6/1993 | Tan | 606/9 |
| 5,304,170 | 4/1994 | Green | 606/9 |
| 5,448,582 | 9/1995 | Lawandy | 372/42 |
| 5,632,741 | 5/1997 | Zavislan et al. | 606/9 |
| 5,707,403 | 1/1998 | Grove et al. | 607/89 |
| 5,721,748 | 2/1998 | Injeyan et al. | 372/3 |
| 5,735,844 | * 4/1998 | Anderson et al. | 606/9 |
| 5,793,781 | * 8/1998 | Lawandy | 372/22 |
| 5,796,761 | 8/1998 | Injeyan et al. | 372/3 |

OTHER PUBLICATIONS

"Stimulated Raman scattering of picosecond pulses in barium nitrate crystals", Petr G. Zverev et al., Optics Communications 97 (1993), 59–64.

"Stimulated Raman scattering of the beam from a copper-–vapor laser in a barium nitrate crystal", S.A. Vitsinskii et al., Quantum Electron, 23 (12), Dec. 1993, 1001–1004.

"Generation of radiation in a resonator under conditions of stimulated Raman scattering in $Ba(NO_3)_2$, $NaNO_3$, and $CaCO_3$, crystals", S.N Karpukhin et al., Sov. J. Quantum Electron., 16(8), Aug. 1986, 1027–1030.

"Conversation of tunable radiation from a laser utilizing an LiF crystal containing $F_2$ color centers by stimulated Raman scattering in $Ba(No_3)_2$ and $KGd(WO_4)_2$ crystals", T.T. Basiev et al., Sov. J. Quantum Electron., 17(12), Dec. 1987, 1560–1561.

"Solid–state barium nitrate Raman laser in the visible region", Chuan He, Thomas H. Chyba, Optics Communications 135 (1997), pp. 273–278.

\* cited by examiner

Primary Examiner—Michael Peffley
(74) Attorney, Agent, or Firm—Ohlandt, Greeley, Ruggiero & Perle, LLP

(57) ABSTRACT

This invention teaches an optical source (10) for performing photomedicine. The optical source includes a Nd:YLF laser (12) having an output providing light having a wavelength of 1.053 micrometers; a frequency doubler (13) that is optically coupled to the laser output for converting a portion of the light to frequency doubled light, the frequency doubler having an output providing frequency doubled light having a wavelength of 526.5 nm; coupled to the output of the frequency doubler, a unit (14) for shifting the frequency doubled light to light having a longer wavelength of about 630 nm; and means (16) for conveying the light having the longer wavelength to the region of tissue. In one embodiment of this invention the shifting unit includes a device for performing stimulated Raman scattering of the frequency doubled light. The invention teaches the optical source and methods for using the optical source for performing photomedicine, such as, for treating a region of tissue to remove port wine stains, to remove a tattoo, and to remove one or more hair follicles, disposed therein.

8 Claims, 1 Drawing Sheet

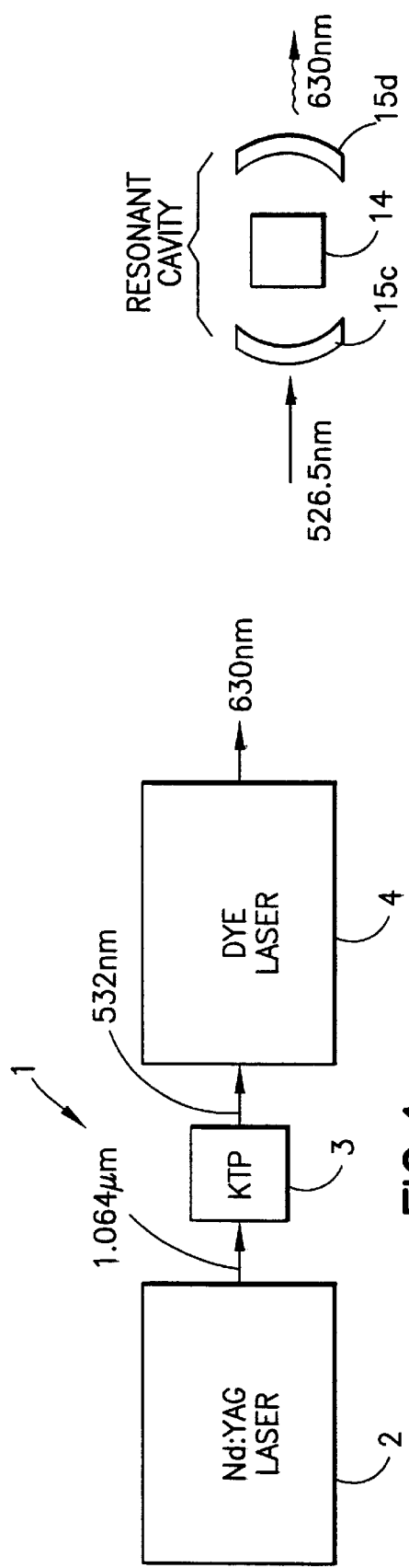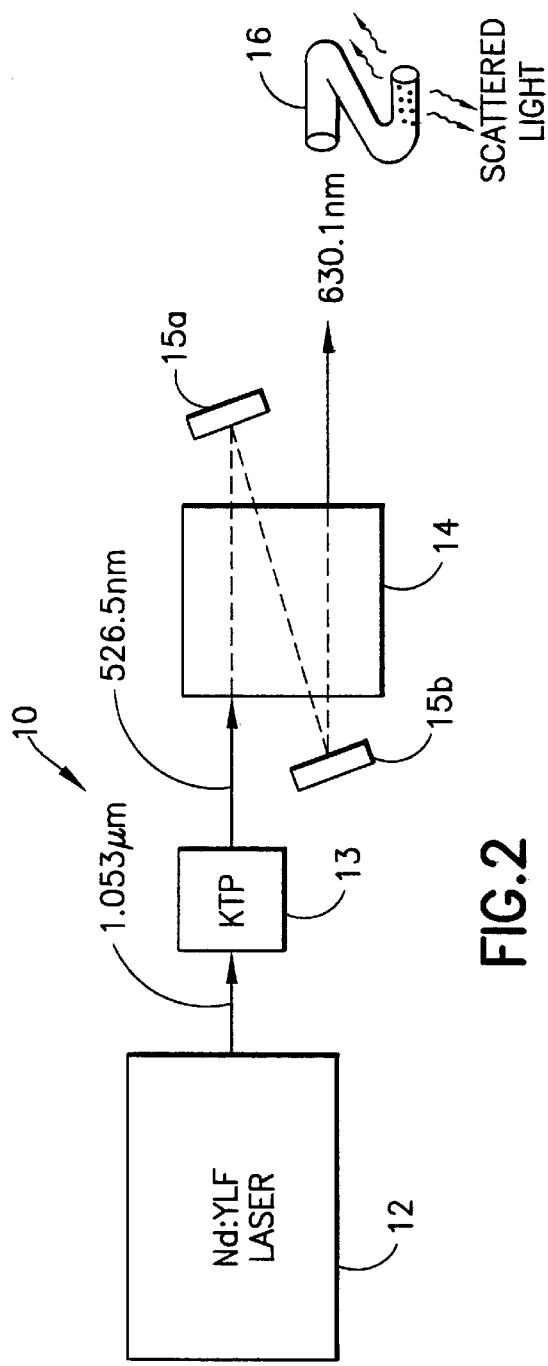

SOLID STATE SOURCE FOR GENERATING INTENSE LIGHT FOR PHOTOMEDICINE

CROSS-REFERENCE TO RELATED APPLICATIONS:

This patent application is a continuation-in-part of copending U.S. Patent Application No.: 08/788,208, filed Jan. 24, 1997, now Pat. No. 5,793,781, entitled "Solid State Source For Generating Intense Light For Photodynamic Therapy And Photomedicine", by Nabil M. Lawandy, the disclosure of which is incorporated by reference herein in its entirety.

FIELD OF THE INVENTION:

This invention relates generally to optically-based therapeutic procedures.

BACKGROUND OF THE INVENTION:

Photodynamic Therapy (PDT) uses specifically designed drugs such as Foscan® (Scotia Pharmaceuticals), ALA (DUSA) and Photofrin (QLT Phototherapeutics) to destroy rapidly dividing cells. These drugs are selectively retained or generated at rapidly dividing cells and are subsequently excited by light to produce the desired effects. The primary mode of activity usually involves energy transfer from these photoexcited drugs to $O_2$ to produce superoxides or $O_2$ in its singlet state. To date this excitation has been provided by lasers, lamps, and new materials such as LaserPaint™ (laser action in amplifying scattering media). Some of these sources are generally expensive and require complicated delivery systems.

Two of the most important photodynamic therapy drugs are the naturally occurring ALA compound and Photofrin. Both of these are porphyrin compounds that have a peak absorption at 630 nm with a linewidth of approximately 35 nm.

Photofrin has recently received FDA approval for the treatment of esophageal cancer. As such, a low cost optical source at 630 nm has become a very important goal.

FIG. 1 illustrates a conventional optical source 1 that is suitable for use with Photofrin and similar photodynamic therapy drugs. The source 1 includes a pulsed (e.g., 150 nanosecond pulse width, 25 KHz pulse repetition rate) Nd:YAG laser 2 that outputs 1.064 μm light to a frequency doubler, such as a KTP crystal 3. A 532 nm output of the KTP crystal 3 is used to drive a dye laser 4, which provides the desired 630 nm light at the required power.

As those skilled in the art will appreciate, the use of the dye laser 4 has a number of disadvantages, including high initial and operating expense, a required use of fluids, pumps and plumbing, and a frequent need for service.

A number of additional photomedicine applications use laser treatment techniques. For example, U.S. Pat. No.: 5,735,844, issued Apr. 7, 1998, entitled "Hair Removal Using Optical Pulses", by Anderson et al., discloses the use of light energy to remove hair follicles within a skin region. U.S. Pat. No.: 5,707,403, issued Jun. 13, 1998, entitled "Method for the Laser Treatment of Subsurface Blood Vessels", by Grove et al., discloses positioning a laser so that light from the laser impinges a selected area of a patient's dermis to selectively destroy blood vessels at a selective depth. Grove et al. further disclose photomedicine applications including the removal of port wine stains, leg veins and hair follicles. Additionally, U.S. Pat. No.: 5,217,455, issued Jun. 8, 1993, entitled "Laser Treatment Method for Removing Pigmentations, Lesions, and Abnormalities from the Skin of a Living Human", by Tan, discloses a laser treatment technique in which successive irradiations of a treatment site on the skin of a patient is performed to remove, in one embodiment, pigmentations representing a tattoo.

It can be appreciated that in each of the above mentioned photomedicine techniques, and others, a low cost, reliable laser source is beneficial. Similarly, it would be beneficial for a single laser system to deliver light having a range of wavelengths over a range of pulse durations.

OBJECTS AND ADVANTAGES OF THE INVENTION:

It is a first object and advantage of this invention to provide a lower cost, essentially solid state optical source providing optical radiation for a photomedicine and/or phototherapeutic application.

It is another object and advantage of this invention to provide a lower cost, essentially solid state optical source providing optical radiation for treating a region of tissue.

It is a further object and advantage of this invention to provide a single laser system which delivers light having a range of wavelengths over a range of pulse durations to a region of tissue.

It is a still further object and advantage of this invention to provide a lower cost, essentially solid state optical source providing optical radiation for treating a region of tissue to remove a port wine stain, a tattoo and hair follicles.

Further objects and advantages of this invention will become more apparent from a consideration of the drawings and ensuing description.

SUMMARY OF THE INVENTION

The foregoing and other problems are overcome and the objects of the invention are realized by methods and apparatus in accordance with embodiments of this invention.

This invention discloses an optical source for performing photomedicine. The optical source includes, by example, a Nd:YLF laser having an output providing light having a wavelength of 1.053 micrometers; a frequency doubler that is optically coupled to the laser output for converting a portion of the light to frequency doubled light, the frequency doubler having an output providing frequency doubled light having a wavelength of 526.5 nm; coupled to the output of the frequency doubler, a unit for shifting the frequency doubled light to light having a longer wavelength in a range of about 600 nm to 1200 nm; and a device for conveying the light having the longer wavelength to a region of tissue. The shifting unit includes a device for performing stimulated Raman scattering of the frequency doubled light.

This invention also discloses a method for providing an optical source for performing photomedicine. The method includes the steps of: (a) providing a Nd:YLF laser capable of emitting light having a wavelength of 1.053 micrometers; (b) phase matching a frequency doubler to the Nd:YLF emission to provide frequency doubled light having a wavelength of 526.5 nm; (c) shifting the frequency doubled light to light having a longer wavelength; and (d) conveying the light having the longer wavelength to the region of tissue.

In accordance with the present invention, the Nd:YLF laser is frequency doubled and then Raman shifted to produce a pump source of suitable wavelengths for a number of photomedicine applications. In one aspect of the present invention, suitable for treatment of subsurface blood vessels to remove port wine stains, the pump source has a wavelength of between 700 nm and 1,100 nm, a fluence of between 5 J/cm² and 100 J/cm², and pulse duration of between 0.2 ms to 100 ms. In a second aspect of the present invention, a region of tissue is treated to remove a tattoo. In the second aspect of the present invention, a suitable pump source has a wavelength of between 600 nm and 1,100 nm, a fluence of between 1 J/cm² and 20 J/cm², and pulse duration of between 10 ns to 300 ns. In a third aspect of the present invention, a region of tissue is treated to remove one or more hair follicles. In the third aspect of the present invention, a suitable pump source has a wavelength of between 680 nm and 1,200 nm, a fluence of between 10 J/cm² and 200 J/cm², and pulse duration of between 50 As to 300 ms.

BRIEF DESCRIPTION OF THE DRAWINGS

The above set forth and other features of the invention are made more apparent in the ensuing Detailed Description of the Invention when read in conjunction with the attached Drawings, wherein:

FIG. 1 is simplified block diagram of a prior art optical source suitable for use in a phototherapeutic application;

FIG. 2 is simplified block diagram of an improved optical source that is constructed in accordance with this invention, the improved source also being suitable for use in a phototherapeutic application; and FIG. 3 illustrates a resonant cavity embodiment of a unit for providing Raman scattering.

Identically labelled elements appearing in different ones of the above described figures refer to the same elements but may not be referenced in the description for all figures.

DETAILED DESCRIPTION OF THE INVENTION

Referring to FIG. 2, in an improved optical source 10 the Nd:YAG laser 1 is replaced with a Nd:YLF laser 12 (i.e., Yttrium Lithium Fluoride (YLiF⁴) in a Nd³⁺ laser host material). The entire laser may be replaced, or the laser 1 of FIG. 1 is retrofitted by removing the Nd:YAG laser rod and replacing same with an equivalent Nd:YLF laser rod.

The Nd:YLF laser 12 operates at 1.053 $\mu$m or 1.064 $\mu$m, and may have a 5–300 nanosecond pulse width and a 10–30 KHz pulse repetition rate. A suitable output power of the Nd:YLF laser is in the range of about 5 W to about 100 W (for 25 KHz operation). The output of the Nd:YLF laser 12 is frequency doubled, such as with a KTP crystal 13 or an equivalent frequency doubler.

The 526.5 nm output of the crystal 13 is then shifted by stimulated Raman scattering or an equivalent technique with a $Ba(NO_3)_2$ (or equivalent) crystal 14 to nominally 630 nm (i.e., 630.1 nm). In one embodiment the Raman shifting is accomplished in a multi-pass configuration (i.e., three passes through the $Ba(NO_3)_2$, or equivalent crystal 14). Thus, mirrors 15a and 15b are provided to establish a suitable multi-pass optical path. It is also within the scope of this invention to accomplish the Raman shifting in a resonant cavity configuration, as shown more particularly in FIG. 3. The 630 nm light (having a power of at least 100 mW to several Watts) is then directed into an optical fiber, catheter, or any suitable device 16 for delivering the 630 nm light to a region to be treated. By example, the device 16 may be a catheter having a scattering region for scattering the 630 nm light at the region of tissue to be treated. In accordance with the present invention, the region of tissue to be treated includes a region of tissue in which a port wine stain, a tattoo and hair follicles are to be removed.

It is noted that light having an appropriate combination of wavelength and pulse duration is chosen according to the nature of the tissue to be treated. That is, light having a suitable wavelength is chosen which can be selectively absorbed by the target tissue and not by the surrounding tissue. The pulse duration of the light is chosen to be short enough to prevent significant heat conduction and possible damage to surrounding tissue, while being long enough to be an effective treatment dosage. Therefore and in accordance with the present invention, the wavelength and the pulse duration of the light use to treat a region of tissue is selectively modified. The selective modification permits tailoring of the wavelength and the pulse duration for a particular clinical application. In FIG. 2, for example, a control signal 18 permits the tailoring of the pulse width of light emitted by the solid-state laser 12, while the crystal 14 permits the tailoring of the wavelength of light output of the crystal 13.

In greater detail, the $Ba(NO_3)_2$ crystal 14 (nominally about 1–5 cm in length) is employed to Raman shift the output of the solid state laser 12 to the required wavelengths for general photomedicine applications and, in particular, to the wavelengths required for photodynamic therapy. The technique relies on the exceptionally high Raman scattering cross-section of $Ba(No_3)_2$ which provides a Stokes shift of 1047 cm⁻¹. This large cross-section is primarily attributed to the narrow linewidth of the transition (approximately 1.5 cm⁻¹) at room temperature. The large cross-section has been used to drive stimulated Raman scattering in centimeter lengths of $Ba(NO_3)_2$ material, both in a single pass and resonant cavity configuration.

General reference may be had in this regard to the following publications: "Stimulated Raman scattering of picosecond pulses in barium nitrate crystals", Petr G. Zverev et al., Optics Communications 97 (1993), 59–64; "Stimulated Raman scattering of the beam from a copper-vapor laser in a barium nitrate crystal", S. A. Vitsinskii et al., Quantum Electron, 23 (12), December 1993, 1001–1004; "Generation of radiation in a resonator under conditions of stimulated Raman scattering in $Ba(N0_3)_2$, $NaNO_3$, and $CaCO_3$ crystals", S. N. Karpukhin et al., Sov. J. Quantum Electron., 16 (8), August 1986, 1027–1030; and "Conversion of tunable radiation from a laser utilizing an LiF crystal containing $F_2$ color centers by stimulated Raman scattering in $Ba(NO_3)_2$ and $KGd(WO_4)_2$ crystals", T. T. Basiev et al., Sov. J. Quantum Electron., 17 (12), December 1987, 1560–1561.

In one embodiment of the invention, a multi-pass configuration is used which allows for the generation of the desired wavelength or wavelengths (e.g., 630.1 nm) by several Stokes Raman conversions (in particular, three Stokes Raman conversions for the photodynamic therapy drug Photofrin). Continuing this process to the fourth Stokes line of 526.5 nm generates 675 nanometers, a wavelength that is expected to be useful for the excitation of the benzoporphyrin derivative (BPD), a photosynthesizer used for prostrate, psoriasis, and macular degeneration conditions.

As was noted previously, a resonant cavity configuration as in FIG. 3 can also be employed. In this embodiment the crystal 14 is disposed between mirrors 15c and 15d, which define a resonant cavity around the crystal 14. Mirror 15c, a dichroic mirror, is transmissive to the input frequency doubled light, and is reflective to the Stokes lines of interest (e.g., lines 1–3 for the 630 nm embodiment and lines 1–4 for the 675 nm embodiment). Mirror 15d is partially transmissive to the Stokes line e.g., third or fourth) that is the desired therapeutic wavelength.

A specific case is the illustrated use of the Nd:YLF laser 12 as a pump source which is then frequency doubled to a 526.5 nm source. A three pass geometry is used to create the third Stokes line at 630.1 nm, with conversion efficiencies exceeding 25%. The 630.1 nm wavelength is an optimum wavelength for Photofrin excitation. Other configurations can be used, such as cavities or multi-pass White cells, to produce the desired wavelengths. These modifications are well within the capabilities of those skilled in the art, when guided by the teachings of this invention.

It can be appreciated that an existing installed base of Nd:YAG lasers can be directly adapted or retrofitted to become pump lasers for generating the desired 630 nm light. The retrofit process may include (a) replacing the Nd:YAG rod in the laser 1 with the Nd:YLF rod, (b) adjusting the KTP crystal for phase matching to the emission from the Nd:YLF rod (by adjusting the KTP crystal angle to about 21°; and (c) placing the $Ba(NO_3)_2$ converter assembly 14, 15a, 15b (or 14, 15c, 15d) after the KTP crystal 13. Using this technique it is possible to obtain, at 630 nm, output powers as high as several watts at kilohertz repetition rates. Such a conversion package is significantly less costly than a dye laser (e.g., by a factor of 12:1), and can be installed in, typically, less than one hour of service time.

The teaching of this invention is also useable with higher pulse energy Nd:YLF lasers which operate at low repetition rates (~30 Hz). These sources provide equivalent average powers at 630 nm, but have the advantage of being very compact and cost effective. The operation of such a higher energy, low repetition rate pulsed Nd:YLF laser, with combined frequency doubling and Raman shifting in $Ba(NO_3)_2$, or any other $R_x(MO_3)_y$ compounds (such as $KNO_3$, $Ca(O_3)$ $Pb(NO_3)$ and $NaNO_3$) can produce other desirable wavelengths for photomedicine directly, or by, serving as a pump source for LaserPaint™ materials (amplifying/scattering media), as described in U.S. Pat. No. : 5,448,582.

Further, and in accordance with the present invention, the Nd:YLF laser 12 is frequency doubled and then Raman shifted to produce a source of suitable wavelengths for a number of photomedicine applications. For example, in one aspect of the present invention suitable for treatment of subsurface blood vessels to remove port wine stains, the source has a wavelength of between 700 nm and 1,100 nm, a fluence of between 5 $J/cm^2$ and 100 $J/cm^2$, and pulse duration of between 0.2 ms to 100 ms.

In a second aspect of the present invention, a region of tissue is treated to remove a tattoo. In the second aspect of the present invention, a suitable source has a wavelength of between 600 nm and 1,100 nm, a fluence of between 1 $J/cm^2$ and 20 $J/cm^2$, and pulse duration of between 10 ns to 300 ns.

In a third aspect of the present invention, a region of tissue is treated to remove one or more hair follicles. In the third aspect of the present invention, a suitable source has a wavelength of between 680 nm and 1,200 nm, a fluence of between 10 $J/cm^2$ and 200 $J/cm^2$, and pulse duration of between 50 $\mu$s to 300 ms.

Conventional treatment methods, for example tattoo removal treatment methods, may require repeated irradiation of the region of tissue to achieve satisfactory treatment results. During each of the repeated irradiations, the timing and the energy density of, and duration of exposure to the laser source may be incrementally increased or decreased.

The incremental increases, or decreases, are made as needed to facilitate the treatment process, i.e. the removal of the tattoo, while minimizing any disfiguring effects, or scaring, within the region of tissue.

In an exemplary tattoo removal process, disclosed in the above-mentioned U.S. patent by Tan, a Q-switched Alexandrite laser apparatus is employed to provide pulse durations of from 1–300 ns, laser beam spot sizes of between 1–100 mm in diameter, light wavelength of about 760 nm, and energy densities (fluence) of between 1–20 $J/cm^2$. Tan teaches a treatment process in which test sites within the region of tissue are identified and successively treated by laser exposure. During each laser treatment the fluence of the laser is adjusted (e.g., increasing it by 0.5–1.0 $J/cm^2$) and, after exposure, the irradiated test site is assessed according to predetermined conditions in order to determine an ideal treatment dosage. Once the ideal treatment dosage is determined, the entire region of tissue may be successively treated to remove the tattoo.

Thus, and in accordance with the present invention, a laser pump source, i.e. the Nd:YLF laser 12 or a Nd:YAG laser, is frequency doubled and then Raman-shifted to produce a source of suitable wavelengths, fluence and pulse duration to accomplish the number of photomedicine applications. That is, the source may be employed to provide a range of wavelengths, fluences and pulse durations to facilitate the treatment of subsurface blood vessels to remove port wine stains, the treatment of a region of tissue to remove a tattoo, and the treatment of a region of tissue to remove one or more hair follicles.

Although described in the context of a Nd:YLF laser, it should be appreciated that the $Nd^{3+}$ laser host material may be doped with other compounds to yield other combinations of emission, frequency doubled, and shifted wavelengths.

As such, and although the presently preferred embodiment of this invention employs the Nd:YLF laser, it is within the scope of this invention to use other lasing materials and harmonics (e.g., 3rd or 4th) in order to obtain a desired wavelength of phototherapeutic light.

It is also within the scope of this invention to employ a diode-pumped laser, such as a diode-pumped YLF laser, as the pump source 12. A diode-pumped YLF operating in the mJ range at kilohertz repetition rates is a suitable choice.

Thus, while the invention has been particularly shown and described with respect to preferred embodiments thereof, it will be understood by those skilled in the art that changes in form and details may be made therein without departing from the scope and spirit of the invention.

What is claimed is:

1. An optical source for treating a region of tissue to remove one or more hair follicles disposed therein, comprising:

a laser having an output providing light having a first wavelength;

a frequency doubler that is optically coupled to said laser output for converting a portion of said light to frequency doubled light, said frequency doubler having an output providing frequency doubled light having a second wavelength;

coupled to said output of said frequency doubler, means for shifting said frequency doubled light to shifted light having a longer wavelength than said second wavelength; and means for conveying said shifted light having said longer wavelength to said region of tissue.

2. An optical source as set forth in claim 1, wherein said shifted light having said longer wavelength is comprised of light having a wavelength in a range of about 680 nm to 1200 nm, a fluence in a range of about 10 $J/cm^2$ to 200 $J/cm^2$, and a pulse duration in a range of about 50 $\mu$s to 300 ms.

3. An optical source as set forth in claim 1, wherein said shifting means is comprised of means for performing stimulated Raman scattering.

4. A method for providing an optical source for treating a region of tissue to remove one or more hair follicles disposed therein, the method comprising the steps of:

providing a laser capable of emitting light having a first wavelength;

phase matching a frequency doubler to the laser emission to provide frequency doubled light having a second wavelength;

shifting the frequency doubled light to shifted light having a longer wavelength than the second wavelength; and conveying the shifted light having the longer wavelength to the region of tissue.

5. A method as set forth in claim 4, wherein the step of shifting includes a step of performing stimulated Raman scattering.

6. A method as set forth in claim 4, wherein the shifted light having the longer wavelength is comprised of light having a wavelength in a range of about 680 nm to 1200 nm, a fluence in a range of about 10 J/cm$^2$ to 200 J/cm$^2$ and a pulse duration in a range of about 50 μs to 300 ms.

7. An optical source for treating a region of tissue to remove one or more hair follicles disposed therein, comprising:

a laser having an output providing light having a first wavelength;

a frequency doubler that is optically coupled to said laser output for converting a portion of said light to frequency doubled light, said frequency doubler having an output providing frequency doubled light having a second wavelength;

coupled to said output of said frequency doubler, a solid state shifter operating in accordance with a plurality of Stokes Raman conversions for shifting said frequency doubled light to shifted light having a longer wavelength than said second wavelength; and means for conveying said shifted light having said longer wavelength to said region of tissue.

8. An optical source as set forth in claim 7, wherein said shifted light having said longer wavelength is comprised of light having a wavelength in a range of about 680 nm to 1200 nm, a fluence in a range of about 10 J/cm$^2$ to 200 J/cm$^2$, and a pulse duration in a range of about 50 μs to 300 ms.

\* \* \* \* \*